United States Patent [19]

Nawaz

[11] Patent Number: 4,861,334
[45] Date of Patent: Aug. 29, 1989

[54] SELF-RETAINING GASTROSTOMY TUBE

[76] Inventor: Arain Nawaz, 620 Belle Terre Rd., Port Jefferson, N.Y. 11777

[21] Appl. No.: 211,254

[22] Filed: Jun. 24, 1988

[51] Int. Cl.⁴ ............................................. A61M 25/00
[52] U.S. Cl. ........................................ 604/49; 604/96; 604/164; 604/178
[58] Field of Search ................. 604/164, 175, 178, 93, 604/96, 97, 51; 128/101, 626

[56] References Cited

U.S. PATENT DOCUMENTS

| | | |
|---|---|---|
| 3,039,468 | 6/1962 | Price . |
| 3,253,594 | 5/1966 | Matthews . |
| 4,077,412 | 3/1978 | Moossun . |
| 4,315,513 | 2/1985 | Nawash et al. ................... 604/175 |
| 4,555,242 | 11/1985 | Saudarar . |
| 4,685,901 | 8/1987 | Parks ................................. 604/96 |
| 4,698,056 | 10/1987 | Ciannella . |

OTHER PUBLICATIONS

Percutaneous Endoscopic Gastrostomy: A Nonoperative Technique for Feeding Gastrostomy–Jeffrey L. Ponsky, MD & Michael W. L. Gauderer, M.D.–Gastrointestinal Endoscopy, vol. 27, No. I, 1981.

Primary Examiner—Stephen C. Pellegrino
Attorney, Agent, or Firm—Leonard Belkin

[57] ABSTRACT

A gastrostomy tube which is retained in place without the use of any stitching. The tube is held in place through the use of a balloon inside the stomach and a collar pressing against the abdominal wall of the patient. The tube is provided with a stretchable section which is lengthened prior to insertion to provide the retention forces required. A trocar is employed to elongate and implant the gastrostomy tube. Also disclosed is a method of implanting a feeding tube.

15 Claims, 1 Drawing Sheet

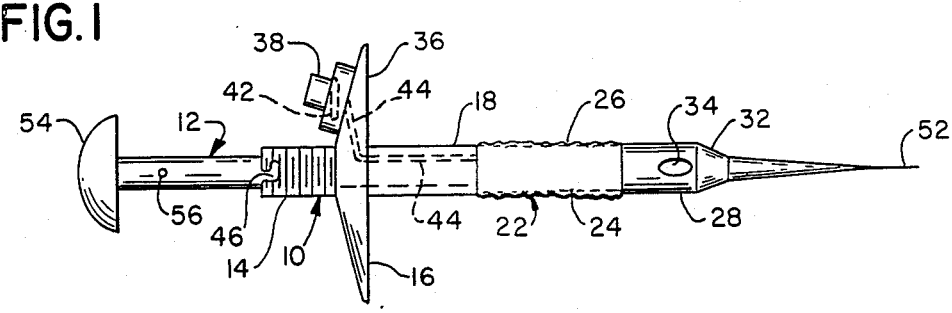
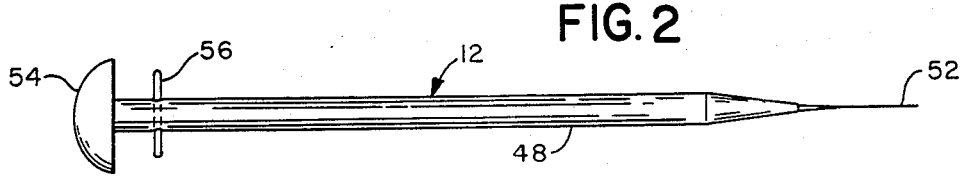
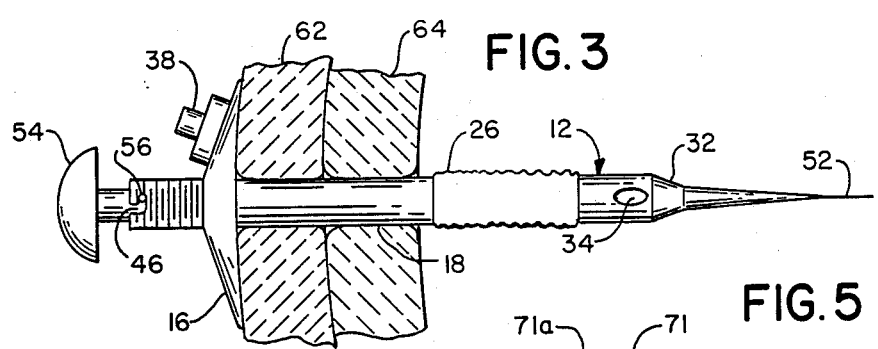
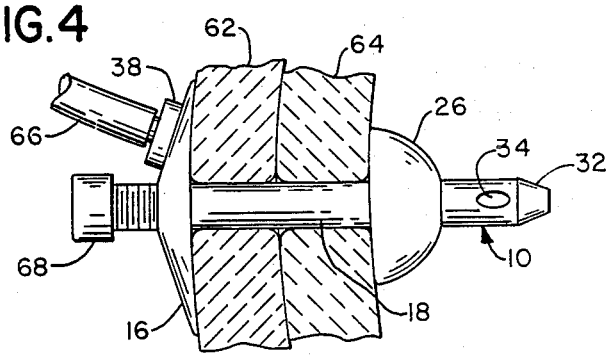
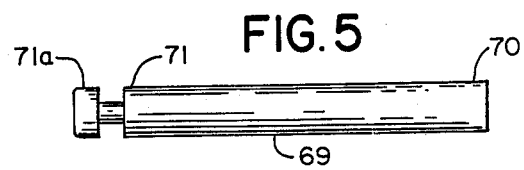
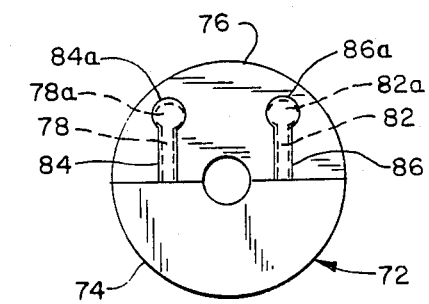
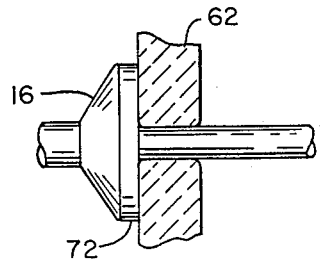

SELF-RETAINING GASTROSTOMY TUBE

BACKGROUND OF THE INVENTION

This invention relates to the field of surgical appliances, and in particular to a gastrostomy tube penetrating the abdominal and stomach walls for feeding a patient by delivery of nourishment into the stomach directly.

Some patients, because of injury, malignancy, birth defects, or nerve damage, may not be able to swallow or otherwise accept nourishment by normal feeding. Many if not most of these patients are subject to such disabilities over an extended period of time so that any installed feeding tube must be able to remain in place during that period of time.

Until some time ago these patients were fed through tubes passing through the nasal passageways or the oral cavities. These procedures were time consuming for medical personnel because the tubes had to be removed and replaced frequently. They were also very uncomfortable for the patients. In addition, the presence of such tubes quite often interfered with other procedures or activities of the patient.

More recently, medical practitioners have resorted to the use of feeding tubes implanted by surgery through the abdominal wall with the end of the tubes terminating within the stomach.

In one such arrangement commonly in use, the outside or proximate end of the tube is capped. When it is time to feed the patient, the cap is removed and the nutrients are flowed under regulation through the tube into the stomach or infused around the clock. While this arrangement has proven to be the most satisfactory approach to date, it does suffer some serious drawbacks.

The procedure to implant such a gastrostomy or feeding tube is quite complex. A gastroscope is introduced through the mouth of the patient into the stomach and a snare is passed through the gastroscope into the stomach. A catheter is implanted surgically through the abdominal wall into the stomach to be surrounded by the snare. A silk suture is passed through the catheter and the snare is tightened around the suture and withdrawn along with the gastroscope. The gastrostomy tube is then pulled through the mouth, esophagus, stomach and out through the abdominal wall. This procedure is described with greater detail in "Percutaneous Endoscopic Gastrostomy: a Nonoperative technique for feeding gastrostomy" by Ponsky et al, *Gastrointestinal Endoscopy*, Vol. 21, No. 1, 1981. When properly placed, the end of the feeding tube outside of the patient is stitched in place to the chest of the patient with the other end of the feeding tube remaining extended into and terminating within the stomach where a balloon may be employed to restrict movement of the feeding tube.

From the description above it is seen that the procedure for installing the feeding tube is very complex. In addition, over a period of time the stitches tend to loosen and furthermore, the arrangement is prone to infection.

Other devices relating to this type of medical apparatus analogous to this invention are shown in U.S. Pat. Nos. 3,039,468, 3,253,594, 4,077,412, 4,555,242, and 4,698,056. There is no teaching or suggestion of the present invention in the prior art as exemplified by the preceding patents.

SUMMARY OF THE INVENTION

The present invention is a gastrostomy or feeding tube which is inserted directly into the stomach of a patient through the abdominal wall. The novel gastrostomy tube of this invention is relatively convenient and safe to install, is self retaining without the need for any stitching, and capable of long term use with little or no foreseeable complications.

In accordance with a preferred embodiment of this invention, the gastrostomy tube comprises a tubular member consisting of a distal end terminating within the stomach, a section adjacent the distal end provided with a balloon, a stretchable section of elastic material passing through the abdominal and stomach walls, and a proximate section terminating out of the abdominal wall. The proximate section includes a shoulder to make contact with and remain flush against the skin of the outside of the abdominal wall without any stitching. The shoulder includes provision for supplying air under pressure to inflate the balloon which makes contact with the interior of the stomach wall. A trocar is employed first to install the tubular member. Upon attaching the trocar to the tube prior to insertion the stretchable section is lengthened and becomes taut. After inflation of the balloon, the trocar is removed causing the stretchable section to retract with the result that the abdominal and stomach walls are squeezed lightly between the inflated balloon and the shoulder thereby retaining the tube in place. The gastrostomy tube is readily removable by deflating the balloon to permit retraction of the appliance.

In order to install the gastrostomy tube described above, a surgical incision is first made at the site of the installation. The gastrostomy tube mounted on the trocar is inserted through the incision into the stomach after the stomach has been examined by a fiber optic endoscope and inflated. The proximate end of the gastrostomy tube is provided with a hooked slot to permit the trocar having a pin properly situated to make positive engagement with the tube prior to placement in order to stretch the tube. The trocar can then be disengaged once the gastrostomy tube is properly placed after the balloon is inflated, and a cap may be utilized to seal off the opening at the proximate end of the tube between feedings.

In order to feed the patient with nutrients, the cap is removed and the nourishment supplied.

It is therefore a principal object of this invention to provide an improved gastrostomy tube which is self-retaining without the need for surgical stitching and which is readily removable.

Other objects and advantages of this invention will hereinafter become obvious from the following detailed description of preferred embodiments of this invention.

BRIEF DESCRIPTION OF THE FIGURES

FIG. 1 is an elevation view of a gastrostomy tube incorporating the principles of this invention along with a trocar, partially inserted, in preparation for implanting in a patient.

FIG. 2 is an elevation view of the trocar shown in FIG. 1.

FIG. 3 shows a section through the abdominal wall of a patient and the trocar engaged with the tube in the process of being implanted.

FIG. 4 is a view similar to that of FIG. 3 with the tube completely installed and the trocar removed.

FIG. 5 is an elevation view of a feeding tube extension.

FIG. 6 is a plan view of a spacer to be used as a shim with the tube shown in the previous figures.

FIG. 7 is a partial section of a view similar to FIG. 3 with a spacer installed.

DETAILED DESCRIPTION OF THE PREFERRED EMBODIMENTS

Referring to FIG. 1, gastrostomy tube 10 is seen as being hollow and consisting of a threaded proximate section 14, a collar 16 to be further described below, a section 18 made up of an elastic material such as rubber, an inflatable section 22 which may consist of a plastic member 24 surrounded by a collapsed balloon 66, and a distal section 28 having a conical terminal portion 32 and one or more ports 34 on the side for a purpose to be later described.

Collar 16 has a flat surface 36 facing the distal end of tube 10 and an air port 38 on its opposite surface. Within port 38 is a check valve 42 which opens under pressure of air being supplied as shown by the arrow but blocks reverse air flow as is understood in the art. Communicating with port 38 is a passageway 44 extending through collar 16 and the outer wall of stretchable section 18 to provide communication with the interior of balloon 26 surrounding member 24. When air under pressure is supplied through port 38 this will cause balloon 26 to expand in a manner to be described below. Check valve 42 prevents balloon 26 from deflating by blocking air flow in the reverse direction.

The proximate end of tube 10 is provided with a pair of hooked slots 46 on opposite sides of tube 10 for a purpose to be described below.

Trocar 12, as best seen in FIG. 2, is an elongated, solid cylindrical body 48 with a pointed distal end 52 engaging distal end 32 of tube 10 (as seen in FIG. 1), and a knob 54 at its proximate end. A locking pin 56 extending through body 48 adjacent knob 54 is sized to engage hooked slots 46 in tube 10. Thus, trocar 12 can make positive engagement with 10 tube by inserting trocar 12 far enough for pin 56 to enter slots 46 and then being rotated counter clockwise to complete the engagement. The length of trocar 12 is such that when it is inserted far enough for pin 56 to engage slots 46 it is necessary to elongate stretchable section 18.

For the manner in which gastrostomy tube 10 would be implanted and employed as a feeding tube, reference is made to FIGS. 3 and 4 where is shown abdominal wall 62 and stomach wall 64 of a patient in which gastrostomy tube 10 is to be implanted.

Initially, the site of the implant is located and the installation procedure monitored using conventional techniques not forming part of this invention. For example, through the oral passageway may be inserted a fiber optic endoscope to light up and view the interior of the stomach and air under pressure to inflate the stomach causing the wall of the latter to press against the abdominal wall as seen in FIG. 3. When the location is selected, an incision is made by a surgeon. This is followed by inserting trocar 12 engaged with tube 10 in a stretched state through the abdominal and stomach walls 62 and 64 as shown in FIG. 3 until collar 16 is flush or almost flush with the outer surface of the abdomen. Then compressed air is delivered through port 38 using a hose 66 and passageway 44 to balloon 26 causing inflation of the latter. Trocar 12 is then removed causing stretchable section to contract causing inflated balloon 26 to press against the inside surface of stomach wall 64 leaving section 18 taut thereby obtaining a light or mild clamping action on walls 62 and 64 between balloon 26 and collar 16, as seen in FIG. 4. It should be pointed out that air port 38 would be provided with a conventional connector so that air hose 66 shown may be connected or disconnected as needed.

Once tube 10 is secured in place, as seen in FIG. 4, tube 10 is ready for use. A cap 68, internally threaded, shown in FIG. 4, may be threaded over the proximate end of tube 10 when the latter is not being used for delivery of nourishment to the interior of the stomach. In the alternative, extension 69 shown in FIG. 5 may be employed for infusion of nutrients over a period of time. The right end 70 of tube 69 would be threaded internally to engage the proximate end of tube 10 whereas the left end 71 would be provided with a LUER-LOK fitting 71a for connection to a pump (not shown) to infuse the nutrients over a period of time. Ports 34 in tube 10 provide alternate discharge paths for the nutrients being supplied in the event that the end of tube 10 is blocked.

Trocar 12 may be made out of stainless steel while tube 10 may be a disposable implement or appliance made completely of plastic material except possibly for stretchable section 18. It would come in different sizes to match as closely as possible the size and condition of the patient. In addition, one or more shim-like spacers may be employed if necessary to insure that there is sufficient tension on tube 10 to insure that it is properly retained in place.

For this purpose there is shown in FIG. 6 a shim-like spacer 72 made out of a pair of segments 74 and 76 with a pair of prongs 78 and 82 extending from segment 74 to snap into openings 84 and 86 in segment 76 when retainer 72 is to be mounted over tube 10 employed between collar 16 and the outer side of abdominal wall 62 as seen in FIG. 7 in order to increase the retention pressure to hold tube 10 in place. Prongs 78 and 82 would have enlarged tips 78a and 82a to snap into enlarged ends 84a and 86a of openings 84 and 86, respectively. One or more of spacers 72 may be employed as required in the event the physician deems that tube 10 is insufficiently secure.

Some of the advantages of this invention include the fact that the procedure involves only a one step entry to the stomach. In addition, the avoidance of the use of stitches limits the opportunity for infection. Also, the removal of the tube simply involves the collapse of the balloon. The simplified procedure also results in less discomfort for the patient.

While only certain preferred embodiments of this invention have been described it is understood that many variations of this invention are possible without departing from the principles of this invention as defined in the claims which follow.

What is claimed is:

1. A self-retaining gastrostomy tube for implantation through the abdominal and stomach walls of a patient, the distal end of said tube to terminate within said stomach and the proximate end of said tube to terminate outside of said patient, comprising:
   a. collar means adjacent the proximate end of said tube for engaging the outer surface of the abdominal wall;
   b. inflatable means mounted on the outside of said tube located within said stomach upon implantation of said tube;

c. said tube including a stretchable section located between said collar means and said inflatable means;
d. trocar means for surgically implanting said tube and elongating said stretchable section during implantation, said stretchable section extending through said abdominal and stomach walls and being elongated and becoming taut during installation of said tube; and
e. means for inflating said inflatable means after implantation of said tube to cause said inflatable means upon inflation to exert a force against the inside surface of said stomach wall transmitted to said collar means on the surface of said abdominal wall whereby said tube is held in place by said collar means and said inflatable means acting on said abdominal and stomach walls as a result of said stretchable section being taut.

2. The gastrostomy tube of claim 1 in which said trocar means engages and elongates said stretchable section, implants said tube, and then disengages and is withdrawn from said tube after said tube is in place and said inflatable means is inflated leaving said stretchable section to retract and exert said force.

3. The gastrostomy tube of claim 1 wherein said inflating means includes port means adjacent the proximate end of said tube for receiving fluid under pressure and a passageway extending from said port means through said stretchable section to the interior of said inflatable means.

4. The gastrostomy tube of claim 3 wherein said inflatable means is a balloon surrounding said tube.

5. The gastrostomy tube of claim 4 wherein said fluid is air.

6. The gastrostomy tube of claim 4 wherein said port means includes check valve means to prevent deflation of said balloon and upon actuation to permit deflation of said balloon to permit removal of said tube.

7. The gastrostomy tube of claim 1 having spacer means between said collar means and said abdominal wall to insure adequate tension on said stretchable section.

8. The method of implanting a tube having a stretchable section in a patient so that the distal end of said tube terminates within an organ of said patient and the proximate end of said tube remains outside of said organ comprising the steps of inserting a trocar through and engaging said tube to cause the elongation of said tube, said tube being surrounded by a balloon adjacent the distal end of said tube, having a collar adjacent the proximate end of said tube, said stretchable section located between said collar and said balloon, said trocar having a pointed end extending out of the distal end of said tube to direct the insertion of said tube, making a surgical incision where said tube is to enter said organ, inserting said trocar with said tube mounted thereon through said incision until said collar is adjacent the outer surface of said organ and elongating said stretchable section, inflating said balloon to press against the inner wall of said organ, and removing said trocar leaving said tube in place and self-retained as a result of said lengthened stretchable section being taut.

9. The method of claim 8 wherein said tube is a gastrostomy tube being implanted through the abdominal and stomach walls of said patient for use in feeding nourishment to said patient.

10. A tube for surgical implantation through one or more organs of a patient, the distal end of said tube terminating within said organ and the proximate end of said tube terminating outside of said organ, comprising:
a. collar means adjacent the proximate end of said tube for engaging the outer surface of said organ;
b. inflatable means mounted on the outside of said tube located within said organ upon implantation of said tube;
c. said tube including a stretchable section of elastic material located between said collar means and said inflatable means;
d. implanting means for lengthening said stretchable section and implanting said tube;
e. means for inflating said inflatable means after implantation of said tube to cause said inflatable means to exert a force against the inside of said organ transmitted to said collar means on the outside of said organ upon release of said implanting means resulting in said tube being held in place by said collar means and said inflatable means.

11. The tube of claim 10 in which said implanting means is a trocar to engage said tube for implanting said tube.

12. The tube of claim 10 wherein said inflatable means is a balloon.

13. The tube of claim 12 wherein said inflating means comprises port means on said collar means for receiving fluid under pressure and passageway means in said tube communicating with said port means and said balloon for delivering said fluid under pressure.

14. The tube of claim 13 having check valve means in said port means for maintaining said balloon inflated and permitting upon actuation the deflation of said balloon in order to remove said tube.

15. The tube of claim 10 having spacer means between said collar means and said organ to insure adequate tension on said stretchable section.

* * * * *